United States Patent
Andreotti et al.

(10) Patent No.: US 7,803,820 B2
(45) Date of Patent: Sep. 28, 2010

(54) 3-TRIAZOLYLTHIAALKYL-3-AZABICYCLO (3-1-O) HEXANES AND THEIR USE AS DOPAMINE D3 RECEPTOR LIGANDS

(75) Inventors: Daniele Andreotti, Verona (IT); Anna Checchia, Verona (IT); Dieter Hamprecht, Verona (IT); Fabrizio Micheli, Verona (IT)

(73) Assignee: Glaxo Group Limited, Middlesex (GB)

( * ) Notice: Subject to any disclaimer, the term of this patent is extended or adjusted under 35 U.S.C. 154(b) by 146 days.

(21) Appl. No.: 11/911,035

(22) PCT Filed: Apr. 12, 2006

(86) PCT No.: PCT/EP2006/003553

§ 371 (c)(1),
(2), (4) Date: Oct. 9, 2007

(87) PCT Pub. No.: WO2006/108700

PCT Pub. Date: Oct. 19, 2006

(65) Prior Publication Data
US 2008/0176917 A1  Jul. 24, 2008

(30) Foreign Application Priority Data
Apr. 14, 2005  (GB) .................................. 0507601.3

(51) Int. Cl.
*A61K 31/41* (2006.01)
*C07D 249/08* (2006.01)
*C07D 257/00* (2006.01)

(52) U.S. Cl. ................. 514/341; 546/272.4; 548/263.2; 548/152

(58) Field of Classification Search ................. 514/341; 546/272.4; 548/263.2, 152
See application file for complete search history.

(56) References Cited

U.S. PATENT DOCUMENTS

| | | | |
|---|---|---|---|
| 2007/0142438 A1* | 6/2007 | Arista et al. ................. 514/341 |
| 2007/0249642 A1 | 10/2007 | Bertani et al. ............... 514/269 |
| 2008/0058398 A1 | 3/2008 | Anderton et al. ............ 514/374 |
| 2008/0167357 A1 | 7/2008 | Hamprecht et al. ......... 514/384 |
| 2008/0227837 A1* | 9/2008 | Arista et al. ................. 514/384 |
| 2008/0242715 A1* | 10/2008 | Capelli et al. ............... 514/384 |
| 2009/0030062 A1 | 1/2009 | Gentile et al. .............. 514/412 |
| 2009/0036461 A1 | 2/2009 | Hamprecht et al. .... 514/252.06 |
| 2009/0124629 A1 | 5/2009 | Bonanomi et al. ..... 514/252.06 |
| 2009/0221593 A1* | 9/2009 | Bonanomi et al. .......... 514/249 |
| 2009/0221618 A1 | 9/2009 | Arista et al. ................. 514/274 |
| 2009/0326011 A1* | 12/2009 | Arista et al. ................. 514/339 |

FOREIGN PATENT DOCUMENTS

| | | | |
|---|---|---|---|
| WO | WO 02/40471 A | | 5/2002 |
| WO | WO 2005/080382 | * | 1/2005 |
| WO | WO 2005/080382 A | | 9/2005 |

OTHER PUBLICATIONS

Patini et al, Chem. Rev., 1996, 96(8), pp. 3147-3176, esp. p. 3150.*
U.S. Appl. No. 11/917,352, filed Jun. 13, 2006, Arista, et al.
U.S. Appl. No. 12/295,024, filed Mar. 30, 2007, Bertani, et al.
U.S. Appl. No. 12/295,304, filed Mar. 30, 2007, Bertani, et al.

* cited by examiner

*Primary Examiner*—Susannah Chung
(74) *Attorney, Agent, or Firm*—James N. Kanagy; Edward R. Gimmi; Charles M. Kinzig

(57) ABSTRACT

The present invention relates to novel compounds of formula (I) or a pharmaceutically acceptable salt thereof:

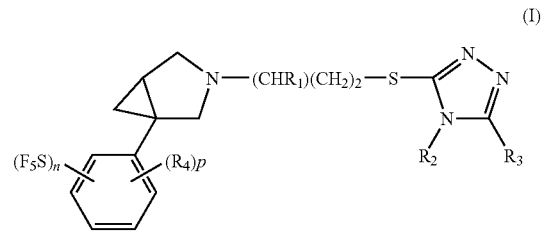

wherein
$R_1$ is hydrogen or $C_{1-4}$alkyl;
$R_2$ is $C_{1-4}$alkyl;
$R_3$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl and $SF_5$;
p is 0, 1, 2, 3 or 4; and
$R_4$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy and $C_{1-4}$alkanoyl;
n is 0 or 1;
wherein when $R_4$ is chlorine and p is 1, such $R_4$ is not present in the ortho position with respect to the linking bond to the rest of the molecule;
and wherein, if n is 0, $R_3$ comprises at least one $SF_5$ group as a substituent;
processes for their preparation, intermediates used in these processes, pharmaceutical compositions containing them and their use in therapy, as modulators of dopamine $D_3$ receptors, e.g. to treat drug dependency, as antipsychotic agents, to treat obsessive compulsive spectrum disorders, premature ejaculation or cognition impairment.

11 Claims, No Drawings

3-TRIAZOLYLTHIAALKYL-3-AZABICYCLO (3-1-O) HEXANES AND THEIR USE AS DOPAMINE D3 RECEPTOR LIGANDS

The present invention relates to novel compounds, processes for their preparation, intermediates used in these processes, pharmaceutical compositions containing them and their use in therapy, as modulators of dopamine $D_3$ receptors.

WO 2002/40471 (SmithKline Beecham) discloses certain benzazepine compounds having activity at the dopamine $D_3$ receptor.

Recently a patent application has been published as WO2005/080382 discloses the following compounds:

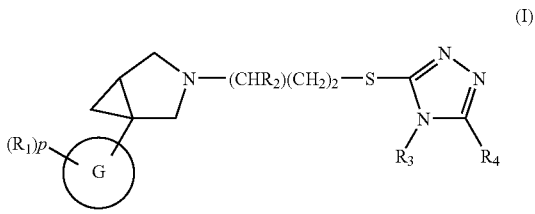

(I)

wherein

G is selected from a group consisting of: phenyl, pyridyl, benzothiazolyl, indazolyl;

p is an integer ranging from 0 to 5;

$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl; or corresponds to a group $R_5$;

$R_2$ is hydrogen or $C_{1-4}$alkyl;

$R_3$ is $C_{1-4}$alkyl;

$R_4$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl;

$R_5$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such a group is optionally substituted by one or two substituents selected from: halogen, cyano, $C_{1-4}$alkyl, halo$C_{1-4}$alkyl, $C_{1-4}$alkoxy, $C_{1-4}$alkanoyl;

and when $R_1$ is chlorine and p is 1, such $R_1$ is not present in the ortho position with respect to the linking bond to the rest of the molecule; and when $R_1$ corresponds to $R_5$, p is 1.

None of the above references disclosed compounds falling into the scope of the present invention.

A new class of compounds which have affinity for dopamine receptors, in particular the dopamine $D_3$ receptor has been found. These compounds have potential in the treatment of conditions wherein modulation of the $D_3$ receptor is beneficial, e.g. to treat drug dependency or as antipsychotic agents.

The present invention provides a compound of formula (I) or a pharmaceutically acceptable salt thereof:

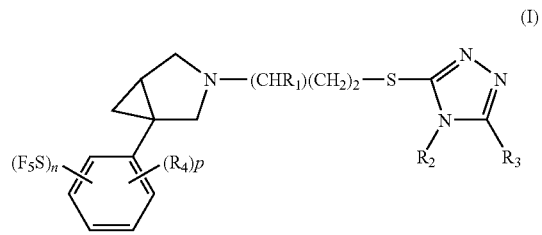

(I)

wherein $R_1$ is hydrogen or $C_{1-4}$alkyl;

$R_2$ is $C_{1-4}$alkyl;

$R_3$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl and $SF_5$;

p is 0, 1, 2, 3 or 4; and $R_4$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy and $C_{1-4}$alkanoyl;

n is 0 or 1;

wherein when $R_4$ is chlorine and p is 1, such $R_4$ is not present in the ortho position with respect to the linking bond to the rest of the molecule;

and wherein, if n is 0, $R_3$ comprises at least one $SF_5$ group as a substituent.

Because of the presence of the fused cyclopropane, compounds of formula (I) are believed to have a "cis" disposition of the substituents (both groups linked to the bicyclic ring system are on the same face of this bicyclic ring system).

In another embodiment of the present invention, compounds of formula (I)' are provided which correspond to the compounds of formula (I) having "cis" disposition, represented by the bold highlight of the bonds:

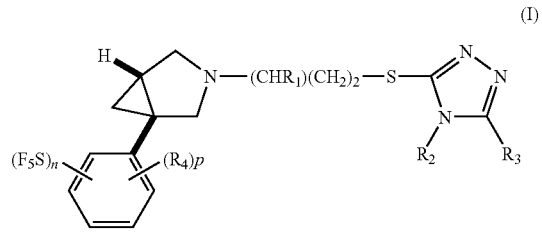

(I)

wherein $R_1$, $R_2$, $R_3$, $R_4$ and p are defined as above for compounds of formula (I).

It will be appreciated that compounds of formula (I)' possess at least two chiral centres, namely at position 1 and 5 in the 3-azabicyclo[3.1.0]hexane portion of the molecule. Because of the fixed cis disposition, the compounds may exist in two stereoisomers which are enantiomers with respect to the chiral centres in the cyclopropane. It will also be appreciated, in common with most biologically active molecules that the level of biological activity may vary between the individual stereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

In compounds of formula (I)' there are at least two chiral centres, which are located in the cyclopropane portion, as depicted below (the bold highlight of the bonds indicates the "cis" configuration):

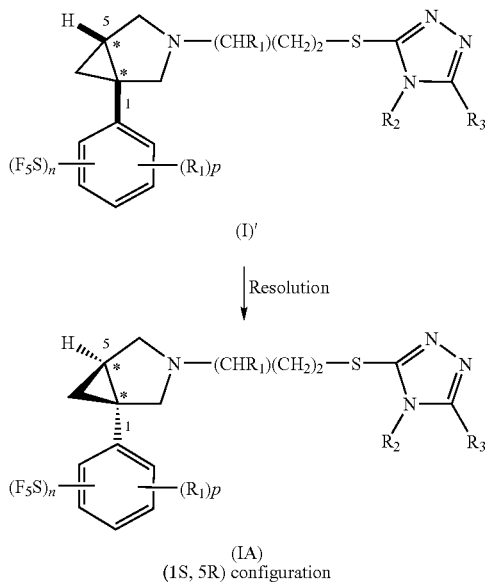

In a further embodiment of the present invention, compounds of formula (IA) are provided that correspond to stereochemical isomers of compounds of formula (I)', enriched in configuration (1S,5R):

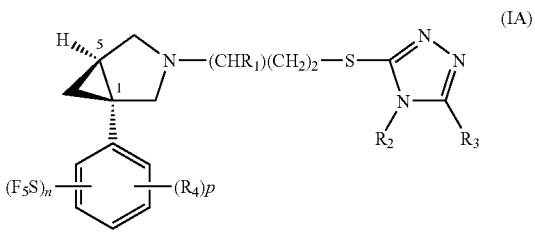

wherein $R_1$, $R_2$, $R_3$, $R_4$ and p are defined as above for compounds of formula (I)' or a pharmaceutically acceptable salt thereof.

It is intended in the context of the present invention that stereochemical isomers enriched in configuration (1S,5R) of formula (IA) correspond in one embodiment to at least 90% e.e. In another embodiment the isomers correspond to at least 95% e.e. In another embodiment the isomers correspond to at least 99% e.e.

The term "5- or 6-membered heteroaromatic group" refers to a monocyclic 5- or 6-membered heterocyclic group containing 1, 2, 3 or 4 heteroatoms, for example from 1 to 3 heteroatoms, selected from O, N and S. When the group contains 2-4 heteroatoms, one may be selected from O, N and S and the remaining heteroatoms may be N. Examples of 5 and 6-membered heteroaromatic groups include pyrrolyl, imidazolyl, pyrazolyl, oxazolyl, isoxazolyl, oxadiazolyl, isothiazolyl, thiazolyl, furyl, thienyl, thiadiazolyl, pyridyl, triazolyl, triazinyl, pyridazinyl, pyrimidinyl and pyrazinyl.

The term "$C_{1-4}$alkyl" refers to an alkyl group having from one to four carbon atoms, in all isomeric forms, such as methyl, ethyl, propyl, isopropyl, butyl, isobutyl, sec-butyl and tert-butyl. The term "n-$C_{1-4}$alkyl" refers to the unbranched alkyls as defined above.

The term "$C_{1-4}$alkoxy" refers to a straight chain or branched chain alkoxy (or "alkyloxy") group having from one to four carbon atoms, such as methoxy, ethoxy, propoxy, isopropoxy, butoxy, isobutoxy, sec-butoxy and tert-butoxy.

The term "$C_{1-4}$ alkanoyl group" as used herein may be a linear or a branched chain alkanoyl group, for example acetyl, ethylcarbonyl, n-propylcarbonyl, i-propyl carbonyl, n-butylcarbonyl or t-butylcarbonyl and the like.

The term "$SF_5$" refers to pentafluorosulfanyl.

The term "halogen" and its abbreviation "halo" refer to fluorine (F), chlorine (Cl), bromine (Br) or iodine (I). Where the term "halo" is used before another group, it indicates that the group is substituted by one, two or three halogen atoms. For example, "halo$C_{1-4}$alkyl" refers to groups such as trifluoromethyl, bromoethyl, trifluoropropyl, and other groups derived from $C_{1-4}$alkyl groups as defined above; and the term "halo$C_{1-4}$alkoxy" refers to groups such as trifluoromethoxy, bromoethoxy, trifluoropropoxy, and other groups derived from $C_{1-4}$alkoxy groups as defined above.

The term "8- to 11-membered bicyclic group" refers to a bicyclic ring system containing a total of 8, 9, 10 or 11 carbon atoms, wherein 1, 2, 3 or 4 or 5 of the carbon atoms are optionally replaced by a heteroatom independently selected from O, S and N. The term includes bicyclic systems wherein both rings are aromatic, as well as bicyclic ring systems wherein one of the rings is partially or fully saturated. Examples of 8- to 11-membered bicyclic groups wherein both rings are aromatic include indenyl, naphthyl and azulenyl. Examples of 8- to 11-membered bicyclic groups having 1, 2, 3, 4 or 5 heteroatoms, in which both rings are aromatic, include: 6H-thieno[2,3-b]pyrrolyl, imidazo[2,1-b][1,3]thiazolyl, imidazo[5,1-b][1,3]thiazolyl, [1,3]thiazolo[3,2-b][1,2,4]triazolyl, indolyl, isoindolyl, indazolyl, benzimidazolyl e.g. benzimidazol-2-yl, benzoxazolyl e.g. benzoxazol-2-yl, benzisoxazolyl, benzothiazolyl, benzisothiazolyl, benzothienyl, benzofuranyl, naphthridinyl, quinolyl, quinoxalinyl, quinazolinyl, cinnolinyl and isoquinolyl. Examples of 8- to 11-membered bicyclic groups having 1, 2, 3, 4 or 5 heteroatoms, in which one of the rings is partially or fully saturated includes dihydrobenzofuranyl, indanyl, tetrahydronaphthyl, indolinyl, isoindolinyl, tetrahydroisoquinolinyl, tetrahydroquinolyl, benzoxazinyl and benzoazepinyl.

The term "heterocyclyl" refers to a 5 or 6-membered monocyclic or 8 to 11-membered bicyclic group wherein 1, 2, 3, 4 or 5 of the carbon atoms are replaced by a heteroatom independently selected from O, S and N and which is partially or fully saturated. Examples of "heterocyclyl" which are fully saturated 5 or 6-membered monocyclic rings include pyrrolidinyl, imidazolidinyl, pyrazolidinyl, isothiazolyl, thiazolyl, tetrahydrofuranyl, dioxolanyl, piperidinyl, piperazinyl, morpholinyl, thiomorpholinyl, tetrahydrothienyl, dioxanyl, tetrahydro-2H-pyranyl and dithianyl. Examples of "heterocyclyl" groups which are partially saturated 5 or 6-membered monocyclic rings include oxazolinyl, isoaxazolinyl, imidazolinyl, pyrazolinyl, 1,2,3,6-tetrahydropyridyl and 3,6-dihydro-2H-pyranyl. Examples of "heterocyclyl" groups which are fully saturated 8 to 11-membered bicyclic rings include decahydroquinolinyl, octahydro-2H-1,4-benzoxazinyl and octahydro-1H-cyclopenta-[b]pyridinyl. Examples of "heterocyclyl" groups which are partially saturated 8 to 11-membered bicyclic rings include 2,3-dihydro-1H-indolyl, 1,2,3,4-tetrahydroquinolinyl, 1,2,3,4-tetrahydroisoquinolinyl and 2,3,4,5-tetrahydro-1H-3-benzazepinyl.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Pharmaceutically acceptable salts are particularly suitable for medical applications because of their greater aqueous solubility relative to the parent compounds. Such salts must clearly have a pharmaceutically acceptable anion or cation. Suitably pharmaceutically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine(N-methylglucamine), lysine and procaine; and internally formed salts. Salts having a non-pharmaceutically acceptable anion or cation are within the scope of the invention as useful intermediates for the preparation of pharmaceutically acceptable salts and/or for use in non-therapeutic, for example, in vitro, situations.

In one embodiment, $R_1$ is hydrogen. In another embodiment $R_1$ is $C_{1-4}$alkyl (e.g. methyl).

In one embodiment, $R_3$ may be optionally substituted phenyl (e.g. phenyl, 4-trifluoromethyl-phenyl, 3,4-difluorophenyl, pentafluorosulfanylphenyl), an optionally substituted bicyclic group such as quinolinyl (e.g. 2-methylquinoline, 8-fluoro-2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl (e.g. 5-chloro-1-methyl-1H-pyrazol-4-yl, 1-methyl-3-trifluoromethyl-1H-pyrazol-4-yl 1,5-dimethyl-1H-pyrazoly-4-yl), an optionally substituted pyrimidyl (e.g. 5-pyrimidinyl), an optionally substituted pyridazinyl (e.g. 4-pyridazinyl), an optionally substituted pyrazinyl (e.g. 5-methyl-2-pyrazinyl), an optionally substituted furanyl (e.g. 3-methyl-2-furanyl, 2,5-dimethyl-3-furanyl), an optionally substituted thienyl (e.g. 5-chloro-2-thienyl), an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl).

In one embodiment, $R_2$ is methyl.

When $R_4$ is chlorine and p is 1, such $R_4$ is not present in the ortho position with respect to the linking bond to the rest of the molecule. In one embodiment, when $R_4$ is $SF_5$ and p is 1, the $SF_5$ group is not present in the ortho position with respect to the linking bond to the rest of the molecule.

In one embodiment, $R_4$ is halogen (such as bromo, fluoro or chloro), hydroxy, cyano, acetyl, trifluoromethyl, trifluoromethoxy, methoxy or tert-butyl.

In one embodiment, p is 0.

In another embodiment p is 1 or 2.

In one embodiment, n is 0.

In another embodiment n is 1.

In one embodiment, a compound of formula (IB) or a pharmaceutically acceptable salt thereof is provided, wherein $R_2$, $R_3$, $R_4$ and p are as defined for formula (I):

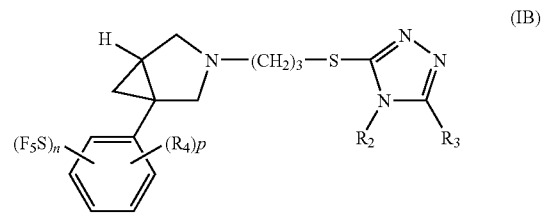

In Formula (IB), in one embodiment, $R_2$ is methyl. $R_3$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$ alkoxy, $C_{1-4}$alkanoyl and $SF_5$; wherein when $R_4$ is chlorine and p is 1, such $R_4$ is not present in the ortho position with respect to the linking bond to the rest of the molecule.

Examples of $R_3$ include an optionally substituted phenyl (e.g. phenyl, 4-trifluoromethyl-phenyl, 3,4-difluorophenyl, pentafluorosulfanylphenyl), an optionally substituted bicyclic group such as quinolinyl (e.g. 2-methylquinoline, 8-fluoro-2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl (e.g. 5-chloro-1-methyl-1H-pyrazol-4-yl, 1-methyl-3-trifluoromethyl-1H-pyrazol-4-yl 1,5-dimethyl-1H-pyrazoly-4-yl), an optionally substituted pyrimidyl (e.g. 5-pyrimidinyl), an optionally substituted pyridazinyl (e.g. 4-pyridazinyl), an optionally substituted pyrazinyl (e.g. 5-methyl-2-pyrazinyl), an optionally substituted furanyl (e.g. 3-methyl-2-furanyl, 2,5-dimethyl-3-furanyl), an optionally substituted thienyl (e.g. 5-chloro-2-thienyl), an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl).

The strategy for determining the absolute configuration of the compounds of the present invention comprised as a first step the preparation of the chiral intermediate, (1S,5R)-1-[4-(trifluoromethyl)phenyl]-3-azabicyclo[3.1.0]hexane (Preparation 11):

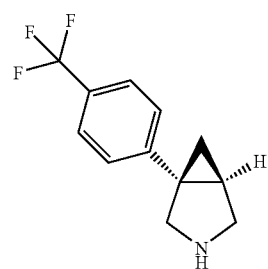

by using (S)-(+) acetyl mandelic acid as resolving agent.

In the literature the absolute configuration of a series of compounds similar to this chiral intermediate is known, see J.

Med Chem 1981, 24(5), 481-90. For some compounds disclosed in the reference, the absolute configuration was proved by single crystal X-ray analysis. Among them, 1-(3,4-dichlorophenyl)-3-azabicyclo[3.1.0]hexane was disclosed.

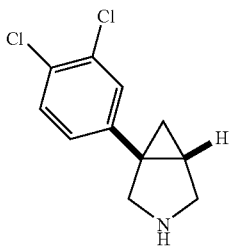

The absolute configuration of the optical isomers of the compounds of the present invention was assigned using comparative VCD (vibrational circular dichroism) and OR (optical rotation) analyses.

The configuration of (1S,5R)-1-(3,4-dichlorophenyl)-3-azabicyclo[3.1.0]hexane was assigned by comparing its experimental VCD spectrum and observed specific rotation to ab initio derived calculated data for (1S,5R)-1-(3,4-dichlorophenyl)-3-azabicyclo[3.1.0]hexane (see Preparation 6) as the reference sample.

The assignment of the absolute configuration of 1-[4-(trifluoromethyl)phenyl]-3-azabicyclo[3.1.0]hexane (Preparation 11) was confirmed by a single crystal X-ray structure obtained from a crystal of (1S,5R)-1-[4-(trifluoromethyl)phenyl]-3-azabicyclo[3.1.0]hexane, (S)-(+)-mandelic acid salt. Both the analysis based on the known configuration of the (S)-(+)-mandelic acid and on the basis of anomalous dispersion effects confirmed the assignment of the title compound as being (1S,5R)-1-[4-(trifluoromethyl)phenyl]-3-azabicyclo[3.1.0]hexane.

For those compounds which were subjected to detailed analysis (VCD; OR included in the experimental details) a common trend was recognised between absolute configuration of the 3-azabicyclo[3.1.0]hexane moiety and measured binding activity at the dopamine D3 receptor for each pair of enantiomers. For the remainder of the compounds of the present invention, where stereoisomers were evaluated separately, absolute configuration was assigned based on a reasonable assumption by a skilled person in the art, i.e. absolute configuration was then assigned based on measured binding activity at the dopamine D3 receptor for both enantiomers and comparison with the data of those compounds which were subjected to detailed analysis.

Chiral molecules exhibit vibrational circular dichroism (VCD). Vibrational circular dichroism (VCD) is the differential interaction of a chiral molecule with left and right circularly polarized infrared radiation during vibrational excitation.

The VCD spectrum of a chiral molecule is dependent on its three-dimensional structure. Most importantly, the VCD spectrum of a chiral molecule is a sensitive function of its absolute configuration and, in the case of flexible molecules, of its conformation. In principle, therefore, VCD permits the determination of the structure of a chiral molecule. VCD spectra were first measured in the 1970s. Subsequently, VCD instrumentation has developed enormously in spectral range and in sensitivity. Currently, VCD spectra of liquids and solutions can be measured over the majority of the fundamental infrared (IR) spectral range ($v \geq 650$ cm$-1$) with high sensitivity at acceptable resolution (1-5 cm$-1$) using both dispersive and Fourier Transform (FT) VCD instrumentation. Very recently, commercial FT VCD instrumentation has become available, greatly enhancing the accessibility of VCD spectra.

The use of VCD as a reliable method for the determination of absolute configuration of chiral molecules is now well established (see for example Shah R D, et al., Curr Opin Drug Disc Dev 2001;4:764-774; Freedman T B, et al., Helv Chim Acta 2002; 85:1160-1165; Dyatkin A B, et al. Chirality 2002; 14:215-219; Solladié-Cavallo A, Balaz M et al., Tetrahedron Assym 2001;12:2605-2611; Nafie L A, et al. Circular dichroism, principles and applications, 2nd ed. New York: John Wiley & Sons; 2000. p 97-131; Nafie L A, et al. in: Yan B, Gremlish H-U, editors. Infrared and Raman spectroscopy of biological materials. New York: Marcel Dekker; 2001. p 15-54; Polavarapu P L, et al., J Anal Chem 2000;366:727-734; Stephens P J, et al., Chirality 2000;12:172-179; Solladié-Cavallo A, et al., Eur J Org Chem 2002: 1788-1796).

The method entails comparison of observed IR and VCD spectra with calculations of the spectra for a specific configuration and provides information both on the absolute configuration and on the solution conformation.

Given an experimental spectrum of a chiral molecule whose absolute configuration and/or conformation are unknown and to be determined, the general procedure is as follows: 1) all possible structures are defined; 2) the spectra of these structures are predicted; and 3) predicted spectra are compared to the experimental spectrum. The correct structure will give a spectrum in agreement with experiment; incorrect structures will give spectra in disagreement with experiment.

VCD spectra are always measured simultaneously with vibrational unpolarized absorption spectra ("infrared (IR) spectra") and the two vibrational spectra together provide more information than does the VCD spectrum alone. In addition, vibrational unpolarized absorption spectra are automatically predicted simultaneously with VCD spectra.

For ab initio assignments, VCD and unpolarized IR spectra were calculated using the Gaussian 98 software package.

When chiral organic molecules are synthesized (or, if natural products, isolated) their optical rotations are routinely measured at one frequency or at a small number of discrete frequencies in the visible-near ultraviolet spectral region. Most commonly, the specific rotation at one frequency, that of the sodium D line, $[\alpha]_D$, is measured. The frequencies used lie below the threshold for electronic absorption, i.e., they are in the "transparent" spectral region. Optical rotation is a reflection of the enantiomeric excess (ee) of the sample and of the absolute configuration (AC) of the predominant enantiomer.

When the optical rotation at a given frequency for 100% ee is available, the measured optical rotation at the same frequency enables the sample ee to be determined. The determination of ee is the predominant application of discrete frequency, transparent spectral region optical rotations. In principle, the AC of the predominant enantiomer, if unknown, can also be determined. However, the determination of AC from optical rotation requires an algorithm which reliably predicts the optical rotations of molecules of known AC and a number of methodologies have been proposed for predicting discrete frequency, transparent spectral region optical rotations (Eliel E L, Wilen S H. Stereochemistry of organic compounds. New York: John Wiley & Sons; 1994. Chapter 13).

Very recently, developments in ab initio Density Functional Theory (DFT) have radically improved the accuracy of optical rotation calculation. As a result, for the first time it has become possible to routinely obtain ACs from optical rotations.

For ab initio OR assignments, the Dalton Quantum Chemistry Program was used.

Further embodiments of the present invention are compounds of formula (IB)' which corresponds to the stereochemical isomers of compounds of formula (IB) as defined above, enriched in configuration (1S, 5R).

In one embodiment, a stereochemical isomer enriched in the (1S,5R) configuration of formula (IB)' or a pharmaceutically acceptable salt thereof is provided, wherein $R_2$, $R_3$, $R_4$, n and p are as defined for formula (I):

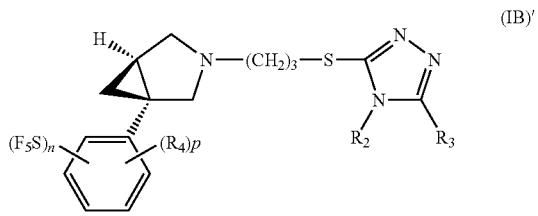

(IB)'

In Formula (IB)', in one embodiment, $R_2$ is methyl. $R_3$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl and $SF_5$; wherein when $R_4$ is chlorine and p is 1, such $R_4$ is not present in the ortho position with respect to the linking bond to the rest of the molecule.

Examples of $R_3$ include optionally substituted phenyl (e.g. phenyl, 4-trifluoromethyl-phenyl, 3,4-difluorophenyl, pentafluorosulfanylphenyl), an optionally substituted bicyclic group such as quinolinyl (e.g. 2-methylquinoline, 8-fluoro-2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl (e.g. 5-chloro-1-methyl-1H-pyrazol-4-yl, 1-methyl-3-trifluoromethyl-1H-pyrazol-4-yl 1,5-dimethyl-1H-pyrazoly-4-yl), an optionally substituted pyrimidyl (e.g. 5-pyrimidinyl), an optionally substituted pyridazinyl (e.g. 4-pyridazinyl), an optionally substituted pyrazinyl (e.g. 5-methyl-2-pyrazinyl), an optionally substituted furanyl (e.g. 3-methyl-2-furanyl, 2,5-dimethyl-3-furanyl), an optionally substituted thienyl (e.g. 5-chloro-2-thienyl), an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl).

Certain of the compounds of the invention may form acid addition salts with one or more equivalents of the acid. The present invention includes within its scope all possible stoichiometric and non-stoichiometric forms.

Pharmaceutical acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) may exist as polymorphs, which are included in the present invention.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms. The present invention includes within its scope all such tautomeric forms, including mixtures.

In one embodiment of the present invention compounds are provided having a molecular weight of 800 or less. In another embodiment compounds are provided having a molecular weight of 600 or less. Generally, and without being limited thereto, such compounds may have higher oral bioavailability, and sometimes higher solubility and/or brain penetrancy. Molecular weight here refers to that of the unsolvated free base compound, excluding any molecular weight contributed by addition salts, solvent (e.g. water) molecules, prodrug molecular parts cleaved off in vivo, etc.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

Example compounds of the present invention include:
3-(3-{[4-methyl-5-(4-methyl-1,3-oxazol-5-yl)-4H-1,2,4-triazol-3-yl]thio}propyl)-(1R,5S/1S,5R)-1-[4-(pentafluoro-$\lambda^6$-sulfanyl)phenyl]-3-azabicyclo[3.1.0]hexane; 3-(3-{[4-methyl-5-(4-methyl-1,3-oxazol-5-yl)-4H-1,2,4-triazol-3-yl]thio}propyl)-(1S,5R)-1-[4-(pentafluoro-$\lambda^6$-sulfanyl) phenyl]-3-azabicyclo[3.1.0]hexane (Example1, Enantiomer 2); (1R,5S/1S,5R)-3-(3-{[4-methyl-5-(4-methyl-1,3-oxazol-5-yl)-4H-1,2,4-triazol-3-yl]thio}propyl)-1-[3-(pentafluoro-$\lambda^6$-sulfanyl)phenyl]-3-azabicyclo[3.1.0]hexane; (1S,5R)-3-(3-{[4-methyl-5-(4-methyl-1,3-oxazol-5-yl)-4H-1,2,4-triazol-3-yl]thio}propyl)-1-[3-(pentafluoro-$\lambda^6$-sulfanyl) phenyl]-3-azabicyclo[3.1.0]hexane (Example 2, Enantiomer 2); (1S,5R)-3-[3-({4-methyl-5-[4-(pentafluoro-$\lambda^6$-sulfanyl) phenyl]-4H-1,2,4-triazol-3-yl}thio)propyl]-1-[4-(trifluoromethyl)phenyl]-3-azabicyclo[3.1.0]hexane; and pharmaceutically acceptable salts thereof.

The present invention also provides a process for preparing a compound of formula (I) or a pharmaceutically acceptable salt thereof as defined above. The process of the present invention comprises the steps of:
(a) reacting a compound of formula (II):

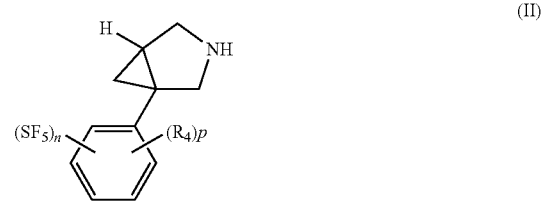

wherein $R_4$, n and p are as defined for formula (I); with a compound of formula (III):

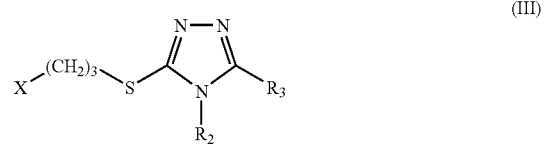

wherein $R_2$ and $R_3$ are as defined for formula (I) and X is a leaving group, or
(b) reacting a compound of formula (IV):

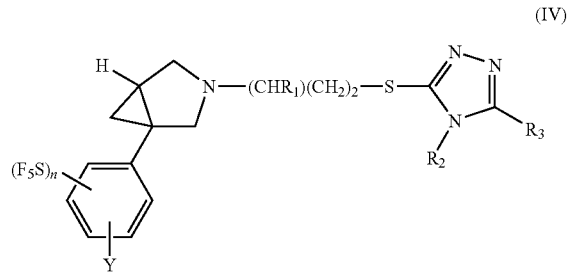

wherein $R_1$, $R_2$, $R_3$ and n are as defined for formula (I) and Y is halogen, a perfluoroalkylsulfonyloxy group (e.g. trifluoromethylsulfonyloxy), or Y is a group M selected from a boron derivative (e.g. a boronic acid function $B(OH)_2$) or a metal function such as trialkylstannyl (e.g. $SnBu_3$), zinc halide or magnesium halide; with a compound $R_4$—Y1, wherein $R_4$ is as defined for formula (I) and Y1 is halogen when Y is a group M; or when Y is halogen or a perfluoroalkylsulfonyloxy group, Y1 is a group M as defined above or hydrogen that can be activated by a suitable base (e.g.

$Cs_2CO_3$) in the presence of a suitable transition metal (e.g. Pd); "leaving group" is as understood by a skilled chemist, i.e. a group which can be displaced by a nucleophile in e.g. a $S_N2$, $S_N1$ or $S_NAr$ type reaction; or (c) reacting a compound of formula (XIV):

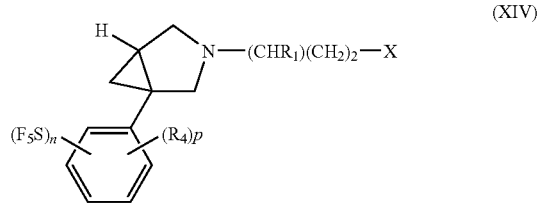

wherein $R_1$, $R_4$, n and p are as defined for formula (I) and X is a leaving group, with a compound of formula (V):

wherein $R_2$ and $R_3$ are as defined for formula (I);
and thereafter optionally for process (a), (b) and (c):
(i) removing any protecting group(s); and/or
(ii) forming a salt; and/or
(iii) converting a compound of formula (I) or a salt thereof to another compound of formula
(I) or a salt thereof.

Process (a) may be performed using conventional methods for the formation of a tertiary amine. The leaving group X can be halogen such as chlorine. Alternatively X can be a sulfonyloxy group such $C_{1-4}$alkylsulfonyloxy (e.g. methanesulfonyloxy), $C_{1-4}$alkylsulfonyloxy or halo$C_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When X is a halogen the reaction may be carried out using a base such as potassium carbonate in the presence of a source of iodide such as sodium iodide in a solvent such as N,N-dimethylformamide at a suitable temperature, e.g. 60° C.

Compounds of formula (II) may be prepared by methods well known in the art (e.g. *J. Med. Chem.* 1981, 24, 481-490). For typical conditions see Preparation 2 hereinafter.

Reaction of a compound of formula (IV) with $R_4$—Y1 according to process (b) may be effected in the presence of a transition metal e.g., palladium catalyst such as bis-triphenylphosphinepalladium dichloride, tetrakis-triphenylphosphinepalladium (0) or the complex formed in situ from tris (dibenzylideneacetone) dipalladium(0) and 4,5-bis (diphenylphosphino)-9,9-dimethylxanthene. When M is a boronic acid function such as $B(OH)_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. When M is hydrogen that can be activated by a suitable base (e.g. $Cs_2CO_3$) in the presence of a suitable transition metal (e.g. Pd) the reaction may be carried out in an inert solvent such as dioxane in the presence of a suitable base such as $Cs_2CO_3$. The substituent Y may be halogen such as bromine, or a sulfonyloxy group such as trifluoromethylsulfonyloxy; and Y1 is may be a group M, such as hydrogen that can be activated by a suitable base (e.g. $Cs_2CO_3$) in the presence of a suitable transition metal (e.g. Pd).

In process (c), a compound of formula (XIV) wherein $R_4$ and p are as defined for formula (I), X is a leaving group and $R_1$ is H (hydrogen) can be prepared by alkylation of a compound of formula (XIII) in the presence of a suitable base such as a tertiary amine, for example diisopropylethylamine, with a propyl derivative carrying two leaving groups of preferably differential reactivity in positions 1 and 3, for example 1-bromo-3-chloropropane. A compound of formula (XIV) wherein X is a leaving group and $R_1$ is $C_{1-4}$alkyl can be prepared by the reaction between a beta-hydroxy ketone, for example 4-hydroxy-2-butanone if $R_1$ is methyl, with a compound of formula (XIII) in the presence of a suitable borohydride source such as $NaBH(OAc)_3$, followed by conversion of the hydroxyl group into a leaving group by methods known to the person skilled in the art, for example by the action of thionyl chloride.

In one aspect of the present invention there is provided a synthetic process for the preparation of compounds of formula (II), comprising the following steps:

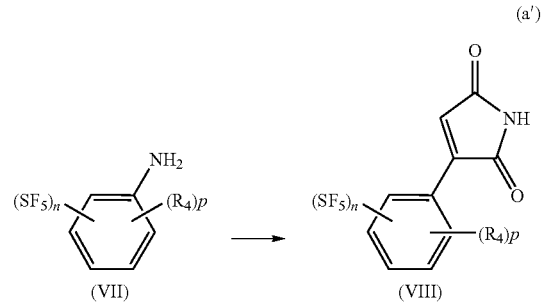

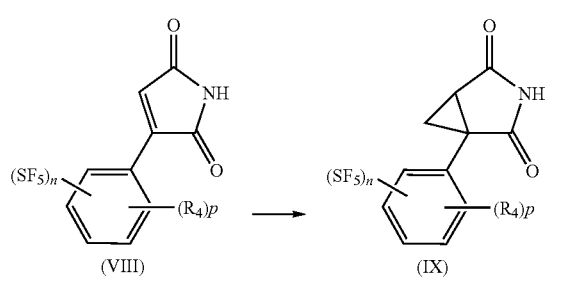

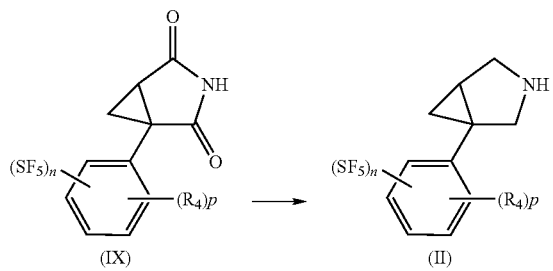

wherein:
- step (a') means diazotation of an aniline (VII) followed by reaction with maleimide to give 3-arylmaleimide (VIII);
- step (b') means cyclopropanation of (VIII) to provide bicyclic imide (IX);
- step (c') means reduction of imide (IX) to give compounds of formula (II).

Step (a') may be effected using conventional methods for the Meerwein reaction (e.g. *J. Am. Chem. Soc.* 1955, 77, 2313 describes the formation of arylmaleimides using this approach). Alternatively, in many cases this step is suitably performed applying a procedure where to a mixture of maleimide, an apropriate copper (II) salt such as anhydrous $CuCl_2$, and a suitable organonitrite, such as tert-butyl nitrite, in a compatible solvent, such as acetonitrile, is slowly added a solution of a compound of formula (VII). This is followed by allowing time to react as appropriate and a suitable workup. Preparation 1 exemplifies this process.

Step (b') consists of slow addition of a solution of purified compound of formula (VIII), or mixtures containing a compound of formula (VIII), dissolved in a suitable solvent such as dimethylsulfoxide, to a solution of trimethylsulfoxonium iodide in a suitable solvent such as dimethylsulfoxide and a suitable base, such as sodium hydride. This is followed by allowing time to react as appropriate and a suitable workup. Preparation 1 exemplifies this process.

Step (c') can be performed using a suitable reducing agent in a compatible solvent, such as borane in tetrahydrofuran or Red-Al® in toluene at an appropriate temperature, such as for example 65° C. in the case of borane as the reducing agent. This is followed by a suitable workup. Preparation 2 exemplifies this process.

In another aspect of the present invention an alternative synthetic process for the preparation of compounds of formula (II), or generally of formula (XIII), is provided. This process comprises the following steps:

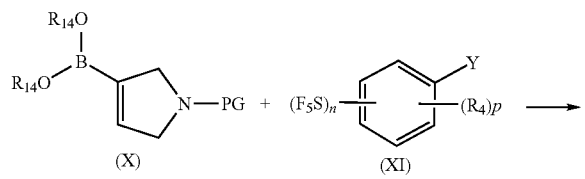

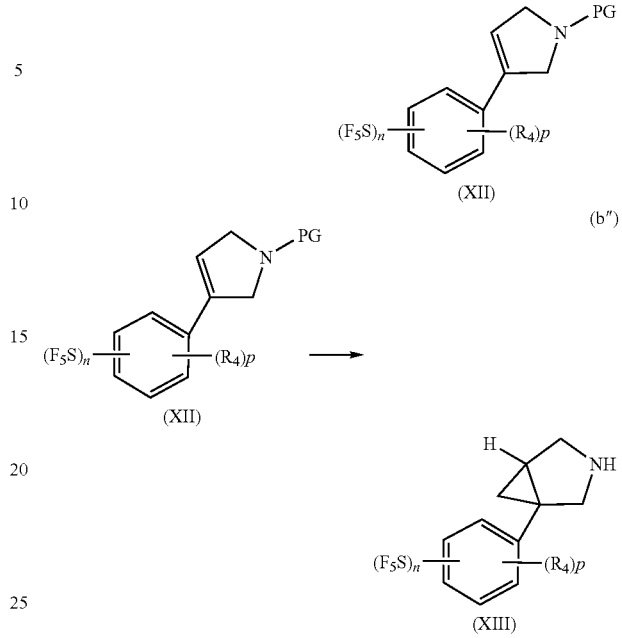

wherein:
$R_{14}O$ is a suitable alkoxy group, PG is an appropriate protecting group and Y may be halogen such as bromine, or a sulfonyloxy group such as trifluoromethylsulfonyloxy and comprising the following steps:
- step (a") means coupling reaction of a (2,5-dihydro-1H-pyrrol-3-yl)boronate (X) with the aromatic halogen or sulfonyloxy derivative (XI);
- step (b") means cyclopropanation of (XII) followed by, if appropriate, deprotection to provide bicyclic amine (XIII).

Step (a") may be effected using conventional methods for the Suzuki coupling, e.g. using tetrakis(triphenylphosphine)palladium(0) as the source of catalytic palladium(0) in the presence of cesium fluoride in an appropriate solvent such as tetrahydrofuran at a suitable temperature. $(R_{14}O)_2B$ may suitably be 4,4,5,5-tetramethyl-1,3,2-dioxaborolan-2-yl and PG benzyl, representing a compound of structure (X) as reported in *Synlett* 2002, 5, 829-831.

Step (b") consists of a cyclopropanation reaction effected for example using the reagent generated from trimethylsulfoxonium iodide and a suitable base such as sodium hydride, in a compatible solvent, for example dimethylsulfoxide.

A compound of formula (III) may itself be prepared by reacting a compound of formula (V):

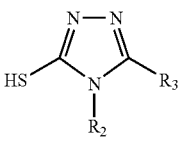

wherein $R_2$ and $R_3$ are as hereinbefore defined; with a compound of formula (VI):

$$L(CHR_1)(CH_2)_2X \qquad (VI)$$

wherein X and $R_1$ are as defined for formula (I) and L is a leaving group, e.g., a bromine atom. For typical reaction conditions, see Preparation 4 hereinafter.

Interconversion reactions between compounds of formula (I) and salts thereof may be performed using methods well known in the art.

Compounds of formula (I) have been found to exhibit affinity for dopamine receptors, in particular the $D_3$ receptor, and are expected to be useful in the treatment of disease states which require modulation of such receptors, such as psychotic conditions. Such affinity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In the context of the present invention pKi (corresponding to the antilogarithm of Ki) is used instead of Ki and the compounds of the present invention typically show pKi greater than 7. In one aspect the present invention provides compounds of formula (I) having a pKi comprised between 7 and 8. In another aspect the present invention provides compounds of formula (I) having a pKi between 8 and 9. In a further aspect the present invention provides compounds of formula (I) having a pKi greater than 9.

Many of the compounds of formula (I) have also been found to have greater affinity for dopamine D3 than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. It has been suggested that blockade of the recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of the present invention are provided which have higher (e.g. $\geq 10\times$ or $\geq 100\times$ higher) affinity for dopamine $D_3$ than dopamine $D_2$ receptors (such affinity can be measured using standard methodology for example using cloned dopamine receptors—see herein). Said compounds may suitably be used as selective modulators of $D_3$ receptors.

From the localisation of $D_3$ receptors, it could also be envisaged that the compounds could also have utility for the treatment of substance abuse where it has been suggested that $D_3$ receptors are involved (e.g. see Levant, 1997, Pharmacol. Rev., 49, 231-252). Examples of such substance abuse include alcohol, cocaine, heroin and nicotine abuse. Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, sexual dysfunction, sleep disorders, emesis, movement disorders, amnesia, aggression, autism, vertigo, dementia, circadian rhythm disorders and gastric motility disorders e.g. IBS.

Other conditions which may be treated with the compounds of the invention include obsessive compulsive (OC) spectrum disorders as below defined.

Compounds of formula (I) may be used for treatment of all aspects of drug dependency including withdrawal symptoms from drugs of abuse such as alcohol, cocaine, opiates, nicotine, benzodiazepines and inhibition of tolerance induced by opioids. In addition, compounds of formula (I) and pharmaceutically acceptable salts and solvates thereof may be used to reduce craving and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the development and maintenance of drug dependence.

The compounds of formula (I) are of potential use as antipsychotic agents for example in the treatment of schizophrenia, schizo-affective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236-242).

Compounds of formula (I) may be used for the treatment of obsessive compulsive disorders (OCD) and of psychiatric and neurospychiatric disorders related to them (OC spectrum disorders).

Compounds of formula (I) may be useful in the treatment of sexual dysfunction, such as premature ejaculation.

Compounds of formula (I) may be useful for the treatment of cognition impairment.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "psychotic disorder" includes:—

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

Within the context of the present invention, the term "substance-related disorder" includes:—

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-induced Persisting Dementia, Alcohol-Induced Persisting Amnestic Disorder, Alcohol-induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); *Cannabis*-Related Disorders such as *Cannabis* Dependence (304.30), *Cannabis* Abuse (305.20), *Cannabis* Intoxication (292.89), *Cannabis* Intoxication Delirium, *Cannabis*-Induced Psychotic Disorder, *Cannabis*-induced Anxiety Disorder and *Cannabis*-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-induced Anxiety Disorder, Cocaine-induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-induced Persisting Dementia, Inhalant-Induced Psychotic Disorder, Inhalant-Induced Mood Disorder, Inhalant-induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

Within the context of the present invention, the term "obsessive compulsive spectrum disorder" includes:

Obsessive compulsive disorders (300.3), somatoform disorders including body dysmorphic disorder (300.7) and hyperchondriasis (300.7), bulimia nervosa (307.51), anorexia nervosa (307.1), eating disorders not elsewhere classified (307.50) such as binge eating, impulse control disorders not elsewhere classified (including intermitted explosive disorder (312.34), compulsive buying or shopping, repetitive self-mutilation, onychophagia, psychogenic excoriation, kleptomania (312.32), pathological gambling (312.31), trichotillomania (312.39) and internet addiction), paraphilia (302.70) and nonparaphilic sexual addictions, Sydeham's chorea, torticollis, autistic disorders (299.0), compulsive hoarding, and movement disorders, including Tourette's syndrome (307.23).

Within the context of the present invention, the term "sexual dysfunction" includes also premature ejaculation (302.75).

Within the present invention the term "cognition impairment" includes cognition impairment in other diseases such as schizophrenia, bipolar disorder, depression, other psychiatric disorders and psychotic conditions associated with cognitive impairment, e.g. Alzheimer's disease.

In a further aspect therefore the present invention provides a method of treating a condition for which modulation [especially inhibition/antagonism (which may also translate into inverse agonism in constitutively active receptor systems)] of dopamine receptors (especially dopamine $D_3$ receptors) is beneficial, which comprises administering to a mammal (e.g. human) in need thereof an effective amount of a compound of formula (I) or a pharmaceutically (i.e physiologically) acceptable salt thereof.

Thus, a still further aspect the invention provides a method of treating a psychotic condition (e.g. schizophrenia) or substance abuse or obsessive compulsive spectrum disorders (such as binge eating) or sexual dysfunctions (such as premature ejaculation) which comprises administering to a mammal (e.g. human) in need thereof an effective amount of a compound of formula (I) as herein defined or a pharmaceutically acceptable salt thereof.

The invention also provides a compound of formula (I) or a pharmaceutically acceptable salt thereof for use in therapy.

The invention also provides a compound of formula (I) or a pharmaceutically acceptable salt thereof for use in the treatment of a condition in a mammal for which modulation [especially inhibition/antagonism (which may also translate into inverse agonism in constitutively active receptor systems)] of dopamine receptors (especially dopamine $D_3$ receptors) is beneficial.

The invention also provides the use of a compound of formula (I) or a pharmaceutically acceptable salt thereof in the manufacture of a medicament for the treatment of a condition in a mammal for which modulation [especially inhibition/antagonism (which may also translate into inverse agonism in constitutively active receptor systems)] of dopamine receptors (especially dopamine $D_3$ receptors) is beneficial.

In one embodiment, $D_3$ antagonists according to the present invention are used in the treatment of psychoses such as schizophrenia, in the treatment of substance abuse, in the treatment of obsessive compulsive spectrum disorders, in the treatment of sexual dysfunction and in the treatment of cognition impairment.

Also provided is the use of a compound of formula (I) or a pharmaceutically acceptable salt thereof in the manufacture of a medicament for the treatment of a psychotic condition (e.g. schizophrenia), substance abuse in a mammal, obsessive compulsive spectrum disorders, sexual dysfunctions and cognition impairment.

Also provided is a compound of formula (I) or a pharmaceutically acceptable salt thereof for use in the treatment of a psychotic condition (e.g. schizophrenia), substance abuse, obsessive compulsive spectrum disorders, sexual dysfunction and cognition impairment in a mammal.

Also provided is a compound of formula (I) or a pharmaceutically acceptable salt thereof for use as an active therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of formula (I) or a pharmaceutically (i.e physiologically) acceptable salt thereof and a pharmaceutically (i.e physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their pharmaceutically acceptable salts which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluoro-chlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the formula (I) or a pharmaceutically acceptable salt thereof calculated as the free base.

The pharmaceutically acceptable compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

Biological Test Methods

Functional potency and intrinsic activity of compounds of this invention can be measured by the following GTPγS scintillation proximity assay (GTPγS-SPA). Cells used in the study are Chinese Hamster Ovary (CHO) Cells.

Cell Line
CHO_D2
CHO_D3

Compounds may be tested according two alternative protocols:

a) Cell membranes are prepared as follows. Cell pellets are resuspended in 10 volumes of 50 mM HEPES, 1 mM EDTA pH 7.4, using KOH. On the day the following proteases are added to the buffer just prior to giving the homogenisation buffer.

$10^{-6}$M Leupeptin (Sigma L2884)–5000×stock=5 mg/ml in buffer 25 ug/ml Bacitracin (Sigma B0125)–1000×stock=25 mg/ml in buffer 1 mM PMSF–1000×stock=17 mg/ml in 100% ethanol $2\times10^{-6}$M Pepstain A–1000×stock=2 mM in 100% DMSO The cells are homogenised by 2×15 second bursts in a 1 litre Glass Waring blender in a class two biohazard cabinet. The resulting suspension is spun at 500 g for 20 mins (Beckman T21 centrifuge: 1550 rpm). The supernatant is withdrawn with a 25 ml pipette, aliquotted into pre-chilled centrifuge tubes and spun at 48,000 g to pellet membrane fragments (Beckman T1270: 23,000 rpm for 30 mins). The final 48,000 g pellet is resuspended in Homogenisation Buffer, (4× the volume of the original cell pellet). The 48,000 g pellet is resuspended by vortexing for 5 seconds and homogenized in a dounce homogenizer 10-15 stokes. The prep is distributed into appropriate sized aliquots, (200-1000 ul), in polypropylene tubes and store at −80° C. Protein content in the membrane preparations is evaluated with the Bradford protein assay.

The final top concentration of test drug is 3 uM in the assay and 11 points serial dilution curves 1:4 in 100% DMSO are carried out using a Biomek FX. The test drug at 1% total assay volume (TAV) is added to a solid, white, 384 well assay plate. 50% TAV of precoupled (for 90 mins at 4° C.) membranes, 5 μg/well, and Wheatgerm Agglutinin Polystyrene Scintillation Proximity Assay beads (RPNQ0260, Amersham), 0.25 mg/well, in 20 mM HEPES pH 7.4, 100 mM NaCl, 10 mM MgCl$_2$, 60 μg/ml saponin and 30 μM GDP is added. The third addition was a 20% TAV addition of either buffer, (agonist format) or EC$_{80}$ final assay concentration of agonist, Quinelorane, prepared in assay buffer (antagonist format). The assay was started by the addition of 29% TAV of GTPγ[$^{35}$S] 0.38 nM final (37 MBq/ml, 1160 Ci/mmol, Amersham). After all additions assay plates are spun down for 1 min at 1,000 rpm. Assay plates are counted on a Viewlux, 613/55 filter, for 5 min., between 2-6 hours after the final addition.

The effect of the test drug over the basal generates EC$_{50}$ value by an iterative least squares curve fitting programme, expressed in the table as pEC$_{50}$ (i.e. −log EC$_{50}$). The ratio between the maximal effect of the test drug and the maximal effect of full agonist, Quinelorane, generates the Intrinsic Activity (IA) value (i.e. IA=1 full agonist, IA<1 partial agonist). fpKi values of test drug are calculated from the IC$_{50}$ generated by "antagonist format" experiment, using Cheng & Prusoff equation: fKi=IC$_{50}$/1+([A]/EC$_{50}$) where: [A] is the concentration of the agonist 5-HT in the assay and EC$_{50}$ is the 5-HT EC$_{50}$ value obtained in the same experiment. fpKi is defined as −log fki.

b) Cell membranes are prepared as follows. Cell pellets are resuspended in 10 volumes of 50 mM HEPES, 1 mM EDTA pH 7.4, using KOH. On the day the following proteases are added to the buffer just prior to giving the homogenisation buffer.

$10^{-4}$M Leupeptin (Sigma L2884)–5000×stock=5 mg/ml in buffer 25 ug/ml Bacitracin (Sigma B0125)–1000×stock=25 mg/ml in buffer 1 mM PMSF–1000×stock=17 mg/ml in 100% ethanol $2\times10^{-6}$M Pepstain A–1000×stock=2 mM in 100% DMSO The cells were homgenised within a glass waring blender for 2×15 secs in 200 mls of 50 mM HEPES+10−4M leupeptin+25 ug/ml bacitracin+1 mM EDTA+1 mM PMSF+2 uM Pepstatin A, (the latter 2 reagents added as fresh ×100 and ×500 stocks respectively in ethanol). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and Pepstatin A. The material was then forced through a 0.6 mm needle, made up to the required volume, (usually ×4 the volume of the original cell pellet), aliquoted and stored frozen at −80 deg C.

The final top concentration of test drug is 3 uM in the assay and 11 points serial dilution curves 1:4 in 100% DMSO are carried out using a Biomek FX. The test drug at 1% total assay volume (TAV) is added to a solid, white, 384 well assay plate. 50% TAV of precoupled (for 60 mins at RT) membranes, 5 μg/well, and Wheatgerm Agglutinin Polystyrene Scintillation Proximity Assay beads (RPNQ0260, Amersham), 0.25 mg/well, in 20 mM HEPES pH 7.4, 100 mM NaCl, 10 mM MgCl2, 60 μg/ml saponin and 30 μM GDP is added. The third addition was a 20% TAV addition of either buffer, (agonist format) or EC80 final assay concentration of agonist, Quinelorane, prepared in assay buffer (antagonist format). The assay was started by the addition of 29% TAV of GTP [35S] 0.38 nM final (37 MBq/ml, 1160 Ci/mmol, Amersham). After all additions assay plates are spun down for 1 min at 1,000 rpm. Assay plates are counted on a Viewlux, 613/55 filter, for 5 min., between 3-6 hours after the final addition.

The effect of the test drug over the basal generates EC50 value by an iterative least squares curve fitting programme, expressed in the table as pEC50 (i.e. −log EC50). The ratio between the maximal effect of the test drug and the maximal effect of full agonist, Quinelorane, generates the Intrinsic Activity (IA) value (i.e. IA=1 full agonist, IA<1 partial agonist). fpki values of test drug are calculated from the IC$_{50}$ generated by "antagonist format" experiment, using Cheng & Prusoff equation: fKi=IC50/1+([A]/EC50) where: [A] is the concentration of the agonist Quinelorane in the assay and EC50 is the Quinelorane EC50 value obtained in the same experiment. fpki is defined as −log fki.

The compounds of the invention listed above have pKi values within the range of 7.0-10.5 at the dopamine D3 receptor. pKi results are only estimated to be accurate to about ±0.3-0.5.

The compounds of the invention listed above have a selectivity over D2 greater than 30.

EXAMPLES

The invention is further illustrated by the following non-limiting examples.

All temperatures refer to ° C. Infrared spectra were measured on a FT-IR instrument. Compounds were analysed by direct infusion of the sample dissolved in acetonitrile into a mass spectra operated in positive electro spray (ES+) ionisation mode. Proton Magnetic Resonance ($^1$H-NMR) spectra were recorded at 400 MHz, chemical shifts are reported in ppm downfield (d) from Me$_4$Si, used as internal standard, and are assigned as singlets (s), broad singlets (bs), doublets (d), doublets of doublets (dd), triplets (t), quartets (q) or multiplets (m).

Experimental vibrational circular dichroism (VCD) spectra were measured using a ChirallR™ VCD spectrometer operating in the 2000-800 cm−1 frequency range. Spectra were measured at room temperature (23° C.) using a sealed transmission cell with barium fluoride windows and a path length of 100 microns. (Scan times varied from 60 to 120 minutes per isomer.) Sample solutions were typically prepared by dissolving 10 milligrams of each enantiomer in 100 microliters of deutero-chloroform (CDCl$_3$). For ab initio assignments, VCD and unpolarized IR spectra were calculated using the Gaussian 98 software package.1.

Optical rotations were measured using a (Perkin Elmer Model 241) polarimeter operating at 589 nm (Sodium source). Measurements were made using a 1 decimeter microcell thermostated at 23° C. Concentrations were typically 10 mg/ml (c=0.01). For ab initio OR assignments, the Dalton Quantum Chemistry Program was used.

Column chromathography was carried out over silica gel (Merck AG Darmstaadt, Germany). The following abbreviations are used in the text: NBS=N-bromosuccinimide, Vitride="Red-Al®", HOBt=1-hydroxybenzotriazole EtOAc=ethyl acetate, Et$_2$O=diethyl ether, DMF=N,N'-dimethylformamide, MeOH=methanol, TFA=trifluoroacetic acid, tetrahydrofuran=tetrahydrofuran, IPA=isopropanol, TEA=triethylamine, DCC=1,3-dicyclohexylcarbodiimide, SCX=strong cation exchanger, Tlc refers to thin layer chromatography on silica plates, and dried refers to a solution dried over anhydrous sodium sulphate, r.t. (RT) refers to room temperature, Rt=retention time, DMSO=dimethyl sulfoxide.

Preparation 1: (1R,5S/1S,5R)-1-[4-(pentafluoro-λ$^6$-sulfanyl)phenyl]-3-azabicyclo[3.1.0]hexane-2,4-dione

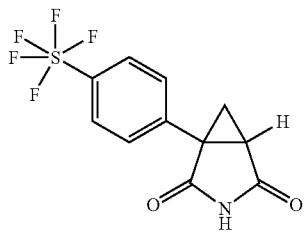

To a slurry of maleimide (2 eq), anhydrous CuCl$_2$ (1.2 eq) and tert-butyl nitrite (1.5 eq) in CH$_3$CN (4.5 mL) at RT a solution of 4-pentafluorosulphonyl aniline (0.5 g) in CH$_3$CN (2.3 mL) was added dropwise. The reaction mixture was stirred at room temperature for 6 h, then HCl (aqueous 6 M, 30 mL) was added. The mixture was extracted with Et$_2$O, the organic layer was washed with 6M HCl, H$_2$O and dried over Na$_2$SO$_4$. The solution was filtered and the filtrate was concentrated in vacuo. By NMR analysis the crude mixture resulted a 1:1 mixture of the arylated maleimide hydrogen chloride adduct (component A) and unreacted maleimide (component B).

A DMSO (7 mL) solution of this crude product was added dropwise to a preformed solution of trimethylsulfoxonium iodide (2 eq with respect to component A plus 2 eq with respect to component B) in anhydrous DMSO (15 mL) to which NaH (3 eq with respect to component A plus 3 eq with respect to component B) had been added portionwise. The reaction mixture was stirred for 1 h, then a saturated NH$_4$Cl solution was added. The reaction mixture was extracted with Et$_2$O and washed with H$_2$O and saturated aqueous NaCl and dried over Na$_2$SO$_4$. The solution was filtered and the filtrate was concentrated in vacuo to give the title compound as colourless oil (0.4 g).

MS (m/z): 313[M]$^+$.

Preparation 2: (1R,5S/1S,5R)-1-[4-(pentafluoro-λ$^6$-sulfanyl)phenyl]-3-azabicyclo[3.1.0]hexane

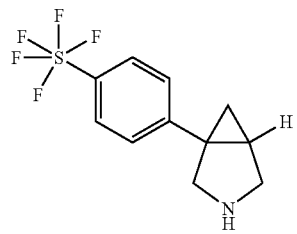

To a solution of (1R,5S/1S,5R)-1-[4-(pentafluoro-λ$^6$-sulfanyl)phenyl]-3-azabicyclo[3.1.0]hexane-2,4-dione (0.381 g) in anhydrous tetrahydrofuran (8 mL), BH$_3$ in tetrahydrofuran (1 M, 2 eq) was added at 0° C. The reaction mixture was stirred at 65° C. for 6 h, then cooled to 0° C. and 6N HCl was added. The mixture was stirred at 65° C. for 2 h and for an additional 18 h at RT. The reaction mixture was concentrated in vacuo, basified to pH 9 with 5N NaOH and extracted with Et$_2$O. The organic layer was washed with saturated aqueous NaCl and dried over Na$_2$SO$_4$. The solution was filtered and the filtrate was concentrated in vacuo. The crude product was purified by ion-exchange chromatography (SCX cartridge 5 g, eluent MeOH/NH$_3$ 0.28M in MeOH) to give the title compound (0.175 g) as a colorless oil.

NMR ($^1$H, CDCl3): δ 7.65 (d, 2H), 7.20 (d, 2H), 3.3-3.0 (m, 4H), 1.75 (m, 1H), 0.95 (m, 2H). MS (m/z): 286 [MH]$^+$.

Preparation 3: (1R,5S/1S,5R)-1-[3-(pentafluoro-λ$^6$-sulfanyl)phenyl]-3-azabicyclo[3.1.0]hexane-2,4-dione

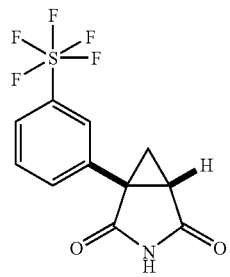

The title compound was prepared from 3-(pentafluoro-λ$^6$-sulfanyl)aniline (500 mg) in analogy to the method described for the Preparation 1 as a crude yellow oil (304 mg), which was used without further purification.

MS (m/z): 313[M]$^+$.

Preparation 4: (1R,5S/1S,5R)-1-[3-(pentafluoro-λ⁶-sulfanyl)phenyl]-3-azabicyclo[3.1.0]hexane

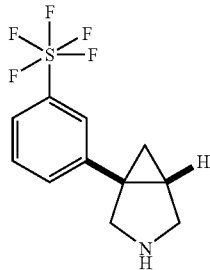

The title compound was prepared in analogy to the method described in Preparation 2 in 155 mg yield as a colourless oil from 1-[3-(pentafluoro-λ⁶-sulfanyl)phenyl]-3-azabicyclo[3.1.0]hexane-2,4-dione (304 mg).

NMR ($^1$H, CDCl$_3$): δ 7.60 (m, 2H), 7.40 (m, 2H), 3.3-3.05 (m, 4H), 1.75 (m, 1H), 0.95 (m, 2H). MS (m/z): 286 [MH]$^+$.

Preparation 5: 4-methyl-5-[4-(pentafluoro-λ⁶-sulfanyl)phenyl]-4H-1,2,4-triazole-3-thiol

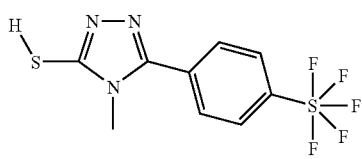

The title compound was prepared in analogy to analogue derivatives described in WO 02/40471 in 150 mg yield as a white solid (40% overall yield) from 4-(pentafluoro-l⁶-sulfanyl)benzoic acid.

NMR ($^1$H, CDCl$_3$): δ 7.92 (d, 2H), 7.75 (d, 2H), 3.70 (s, 3H).

MS (m/z): 315 [M]$^-$.

Preparation 6: (1R,5S/1S,5R)-1-(3,4-Dichlorophenyl)-3-azabicyclo[3.1.0]hexane

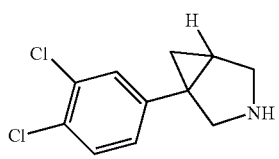

The crude title compound was prepared in 0.36 g yield from commercially available methyl 3,4-dichlorophenylacetate (1 g, 4.57 mmol) following the methods described below:

Preparation 6a: Methyl bromo(4-methoxyphenyl)acetate

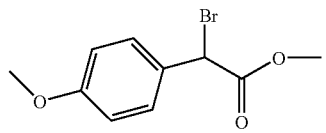

To a mixture of methyl 4-methoxyphenylacetate (20 g, 0.11 mol) and NBS (0.11 mol) in CCl$_4$ (0.2 l) were added 3 drops of 48% HBr and this mixture was heated to reflux for 8 h. The cooled solution was filtered through a pad of silica gel and the filtrate was evaporated in vacuo to give 29 g of the title compound as pale yellow oil, which was used in the subsequent step without further purification.

NMR ($^1$H, CDCl$_3$): δ 7.3 (d, 2H), 6.8 (d, 2H), 5.1 (s, 1H), 3.8 (s, 3H), 3.5 (s, 3H).

Preparation 6b: Dimethyl 1-(4-methoxyphenyl)-1,2-cyclopropanedicarboxylate

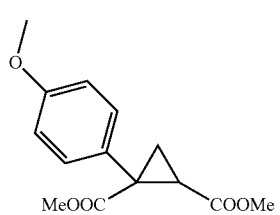

To a stirred slurry of NaH (4.4 g, 60% in mineral oil) in anhydrous Et$_2$O (0.3 l) was added methanol (10.3 mL) followed by a solution of bromo ester obtained in Prep. 3a, methyl bromo(4-methoxyphenyl)acetate (29 g) in methyl acrylate (19.8 mL) (for examples starting from an ethyl phenylacetate derivative ethanol and ethyl acrylate were used, respectively) and methanol (3 mL) at 0° C., over a 30 min. The mixture was stirred at 25° C. for 24 h and then unreacted NaH was decomposed with 3 mL methanol. Water was added (75 mL), the organic phase separated, dried over Na$_2$SO$_4$ and filtered. Volatiles were evaporated in vacuo to give 31.5 g of the title compound as an oil, which was used in the subsequent step without further purification.

NMR (¹H, CDCl₃): δ 7.3 (d, 2H), 6.8 (d, 2H), 3.77 (s, 3H), 3.73 (s, 3H), 3.64 (s, 3H), 2.18 (dd, 1H), 2.05 (dd, 1H), 1.46 (dd,1H). MS (m/z): 265.4[MH]⁺.

Preparation 6c:
1-(4-Methoxyphenyl)-1,2-cyclopropanedicarboxylic acid

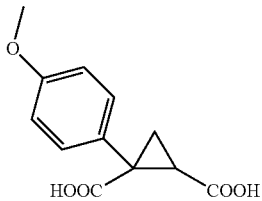

A mixture of diester obtained in Prep. 3b (31.5 g) and KOH (13.5 g) in 1:1 EtOH:H₂O (240 mL) was heated at reflux for 6 h and then concentrated to half the original volume. The aqueous solution was extracted with Et₂O, chilled in ice, and then made acidic with 25 mL of 12N HCl. White crystalline product was collected by filtration and dried under vacuo to give 12.8 of the title compound (overall yield from methyl bromo(4-methoxyphenyl)acetate: 50%).
NMR (¹H, DMSO): δ 12.5 (bs,2H), 7.25 (d, 2H), 6.85 (d, 2H), 3.7 (s, 3H), 2.0 (dd, 1H), 1.85 (dd, 1H), 1.38 (dd, 1H). MS (m/z): 235.0[M−H]⁻.

Preparation 6d: (1R,5S/1S,5R)-1-[4-(Methoxy)phenyl]-3-azabicyclo[3.1.0]hexane-2,4-dione

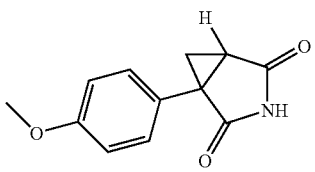

A mixture of 12.8 g of the diacid obtained in Preparation 3c and 6.5 g of urea in 300 mL of m-xylene was heated at reflux for 8 h and then concentrated to dryness in vacuo. The crude was purified by column chromatography (AcOEt:cyclohexane=1 (?):10 to 4:6) to give 5.5 g of the title compound (y=46%).
MS (m/z): 218.1 [MH]⁺.

Preparation 6e: (1R,5S/1S,5R)-1-(4-Bromophenyl)-3-azabicyclo[3.1.0]hexane

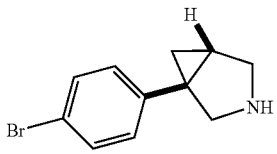

To 20 mL of 1M BH₃-tetrahydrofuran, stirred at 0° C. under N₂, was slowly added a solution of 1.32 g (5 mmol) of (1R,5S/1S,5R)-1-(4-bromophenyl)-3-azabicyclo[3.1.0]hexane-2,4-dione in 20 mL of dry tetrahydrofuran. This solution was stirred at room temperature for 15 min and then warmed on a steam bath for 1 h. The solution was then cooled in an ice bath, 2.5 mL of 6 M HCl was added cautiously, and the solvent was removed in vacuo. The residual material was combined with 12.5 mL of 5 M NaOH and the mixture was extracted with ether. The ether extract was washed twice with water, dried over Na₂SO₄ and filtered to give 1.19 g of the title compound (y=100%).
NMR (¹H, CDCl₃): δ 7.35 (d, 2H), 7.02 (d, 2H), 3.25-2.96 (m, 4H), 1.63 (dd, 1H), 1.55 (dd, 1H), 1.30 (dd, 1H), NH not observed. MS (m/z): 238.1[MH]⁺, 1Br.

(1R,5S/1S,5R)-1-(3,4-Dichlorophenyl)-3-azabicyclo [3.1.0]hexane was separated to give the separated enantiomers by preparative chromatography using a chiral column chiralcel AD 10 um, 250×21 mm, eluent A: n-hexane; B: isopropanol+0.1% isopropyl amine, gradient isocratic 2% B, flow rate 7 mL/min, detection UV at 200-400 nm. Retention times given were obtained using an analytical HPLC using a chiral column chiralcel AD 5 um, 250×4.6 mm, eluent A: n-hexane; B: isopropanol +0.1% Isopropyl amine, gradient isocratic 2% B, flow rate 1.2 mL/min, detection UV at 200-400 nm.

Enantiomer 1, (1R,5S)-1-(3,4-dichlorophenyl)-3-azabicyclo[3.1.0]hexane, was recovered in 20 mg yield as white solid from the racemate (60 mg). Rt.=41 min.

Enantiomer 2, (1S,5R)-1-(3,4-dichlorophenyl)-3-azabicyclo[3.1.0]hexane, was recovered in 28 mg yield as white solid from the racemate (60 mg). Rt.=43.4 min.

The absolute configuration of (1S,5R)-1-(3,4-dichlorophenyl)-3-azabicyclo[3.1.0]hexane was assigned using ab initio VCD and ab initio OR analyses.

Specific Optical Rotation of (1S,5R)-1-(3,4-dichlorophenyl)-3-azabicyclo[3.1.0]hexane: [α]_D=−67.9° (CDCl₃, T=20° C., c≈0.01 g/mL).
NMR (¹H, CDCl₃): δ 7.35 (d, 1H), 7.27 (s, 1H), 7.02 (dd, 1H), 3.25 (d, 1H), 3.13 (bm, 2H), 3.06 (d, 1H), 1.71 (m, 1H), 0.93 (m, 2H), NH not observed. MS (m/z): 228 [MH]⁺, Preparation 7: 3-[(3-Chloropropyl)thio]-4-methyl-5-(4-methyl-1,3-oxazol-5-yl)-4H-1,2,4-triazole

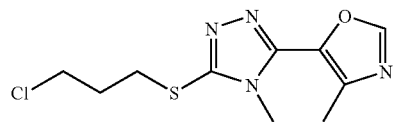

Ethyl-2-chloroacetoacetate (1 wt; 1 eq., 1000 g) was aged with formamide (0.68 vol; ca. 2.8 eq.) and the resulting solution was heated to 120° C. After 5 hours the mixture was allowed to cool to room temperature and allowed to age under nitrogen over night. The mixture was treated with NaOH (3 M, 6 vol, reaction moderately exothermic) and stirred at room temperature for 4 hours. Ethyl acetate (6 vol) was added and the phases allowed to separae. The organic layer was discarded while the aqueous was acidified with conc. (32%) aqueous HCl to pH 2 (ca. 2.0 vol). A precipitate started to form. The suspension was treated with AcOEt (8 vol) and vigorously stirred until the bulk of the precipitate had dissolved. The aqueous phase was further extracted with AcOEt twice (6 vol each) and the combined organic layers distilled to low volume (again a suspension was observed at low volume). Fresh AcOEt (8 vol) was added and the mixture evaporated to dryness. The collected solid was placed in the oven at 40° C. over night under reduced pressure to give 4-methyl-1,3-oxazole-5-carboxylic acid (498 g, 64.5%).

This material (498 g, 1 wt) was dissolved in dry tetrahydrofuran (5 vol), under nitrogen, cooled to 0° C. DCC (1.62 wt, 1 eq) was added portionwise followed by HOBt (1.07 wt, 1 eq). The mixture was warmed to 25±2° C. and stirred for 30 min. 4-Methyl-3-thiosemicarbazide (0.83 wt, 1 eq) was then added and the mixture further stirred for 2 h at 25±2° C. The mixture was filtered and the cake was washed with fresh tetrahydrofuran (1 vol) and dried on the filter for a few hours. The cake was suspended in 1 M aqueous NaOH (13 vol) and heated to 70° C. for 30 min. After this time, the mixture was cooled to 25±2° C. and a solid was removed by filtration. The cake was washed with 1 M aqueous NaOH (10 vol). The combined mother liquors were cooled to 0° C. and acidified to ca. pH 5 with HCl (aqueous, 16%; NOTE: keep temperature while adding HCl below +10° C.). The suspended product was isolated by filtration washing with water (2×3 vol). The cake was dried at 40° C. for 18 h in high vacuum to obtain 4-methyl-5-(4-methyl-1,3-oxazol-5-yl)-2,4-dihydro-3H-1,2,4-triazole-3-thione (respectively a tautomeric form thereof; 290 g, 37%).

NaOEt (21% solution in EtOH, 2.08 vol, 1.1 eq) was added to EtOH (20 vol) under nitrogen atmosphere. 4-Methyl-5-(4-methyl-1,3-oxazol-5-yl)-2,4-dihydro-3H-1,2,4-triazole-3-thione (respectively a tautomeric form thereof; 290 g, 1 wt) was added in one portion and the resulting mixture stirred at 25±2° C. until a clear solution-was obtained. Then 1-bromo-3-chloropropane (0.54 vol, 1.1 eq) was added and the solution stirred at 40° C for 24 h then cooled to 25° C. After filtration water (20 vol) was added and the ethanolic phase was removed by vacuum distillation (internal temperature ~40° C). The mixture was extracted with EtOAc (41 vol). The aqueous layer was removed and the organic phase was evaporated to dryness. Dichloromethane (4 vol) was added. The organic solution is purified through a short silica gel column (18 wt of silica), eluting with EtOAc (200 vol) to give the title compound as a solid foam (267.64 g, 66%).

NMR (¹H, CDCl₃): δ 7.90 (s, 1H), 3.70 (s, 5H), 3.40 (t, 2H), 2.52 (s, 3H), 2.30 (m, 2H),

Preparation 8:
3-[4-(Trifluoromethyl)phenyl]-1H-pyrrole-2,5-dione

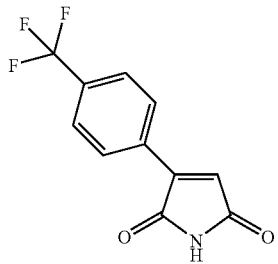

A mixture of hydrochloric acid (37%, 285 mL) and water (190 mL) was added to 4-(trifluoromethyl)aniline (150 g, 116 mL) at room temperature with vigorous stirring and the formed precipitate was allowed to stir for further 30 minutes. Temperature was reduced to 0° C. and sodium nitrite (70.6 g) in 180 mL of water was added dropwise to the stirred suspension. At the end of diazotisation, a clear yellow solution was obtained. Maleimide (180 g) in acetone (1.1 l) was added dropwise at 0° C. and then the pH of the solution was adjusted to 3-3.5 by adding sodium acetate. Copper (II) chloride (18.8 g) was added to the vigorously stirred mixture. After a few minutes a gas started to develop (conspicuous foaming). The reaction mixture was allowed to stir at 0° C. for 1 h and overnight at room temperature.

Acetone was removed in vacuo, the residue was filtered and dried overnight in vacuo to give the title compound (155 g) as a light brown solid (y=63%).

MS (m/z): 242.2 [MH]⁺.

Preparation 9: (1R,5S/1S,5R)-1-[4-(Trifluoromethyl)phenyl]-3-azabicyclo[3.1.0]-hexane-2,4-dione

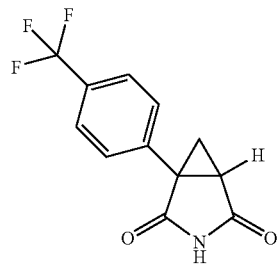

Milled sodium hydroxide (40 g) was added in small portions to a stirred solution of trimethylsulfoxonium iodide (219 g) in DMSO (anhydrous, 2 l). The resulting mixture was allowed to stir at room temperature for 1.5 h.

3-[4-(Trifluoromethyl)phenyl]-1H-pyrrole-2,5-dione (Preparation 8, 120 g) dissolved in DMSO (anhydrous, 0.5 l) was then added dropwise and the resulting mixture was allowed to stir at room temperature for 20 minutes. Temperature was then reduced to 0° C. and NH₄Cl (aqueous saturated solution, 2 l) was slowly added, followed by Et₂O (1 l). After separation of the two phases, the aqueous layer was repeatedly extracted with Et₂O (3×1 l). Combined organic layers were washed with brine (2×1 l) and then dried over Na₂SO₄. Evaporation of the solvent gave a light brown solid which was suspended in 1 l of dichloromethane and 1 l of cyclohexane. The mixture was allowed to stir at room temperature for 45 minutes and then filtered to give the title compound (116 g) as white solid (y=71%).

MS (m/z): 256.1 [MH]⁺.

Preparation 10: (1R,5S/1S,5R)-1-[4-(Trifluoromethyl)phenyl]-3-azabicyclo[3.1.0]-hexane

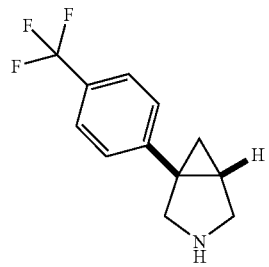

Borane (1M in tetrahydrofuran, 1.4 l) was charged into a 5 l reactor under N₂ and cooled at 0° C. (1R,5S/1S,5R)-1-[4-(Trifluoromethyl)phenyl]-3-azabicyclo[3.1.0]hexane-2,4-dione (Preparation 9, 101 g) dissolved in tetrahydrofuran (anhydrous, 1 l) was then added dropwise with vigorous stirring whereby the temperature was constantly kept below 5° C. and gas evolution was monitored. At the end of the addition the resulting mixture was allowed to stir at 0° C. for 1 h and then at room temperature overnight.

The mixture was then cooled to 0° C. and methanol (200 mL) followed by hydrochloric acid (6 M solution, 0.8 l) were cautiously added monitoring gas evolution. tetrahydrofuran was then removed in vacuo, the residue was cooled to 0° C. and sodium hydroxide (5 M solution) was added until pH 9-10 had been reached. The aqueous layer was extracted with Et$_2$O (3×1 l). Removal of solvent in vacuo gave the title compound (140 g) as colorless oil.
MS (m/z): 228.1 [MH]$^+$.

Preparation 11:(1S,5R)-1-[4-(Trifluoromethyl)phenyl]-3-azabicyclo[3.1.0]hexane

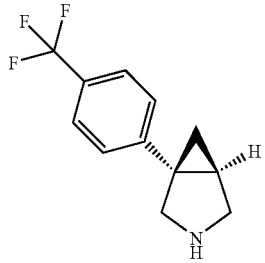

(S)-(+)-Mandelic acid (94 g) was added in portions to a stirred solution of (1R,5S/1S,5R)-1-[4-(trifluoromethyl)phenyl]-3-azabicyclo[3.1.0]hexane (Preparation 10, 140 g) in 1.4 l of tetrahydrofuran. The resulting mixture was stirred at room temperature for 2 h until a white precipitate was formed. The mixture was then warmed up to reflux temperature, stirred for 45 minutes and then slowly cooled down to room temperature. The white solid was collected by filtration and dried in vacuo. This material was recrystallised 4 times from tetrahydrofuran (10 volumes) to give 32.5 g of a white solid. This material was then suspended in sodium hydroxide (1M solution, 400 mL) and Et$_2$O (400 mL) and allowed to stir at room temperature until complete dissolution. After separation of the two phases, the aqueous layer was extracted again with Et$_2$O (3×250 mL). Combined organic layers were washed with sodium hydroxide (1M solution, 3×200 mL) and then dried over Na$_2$SO$_4$. Evaporation of solvent in vacuo gave the title compound (19 g) as white solid (y=37%).

The absolute configuration of the optical isomers was assigned using comparative VCD (vibrational circular dichroism) and OR (optical rotation) analyses.

The configuration of the title compound was assigned by comparing its experimental VCD spectrum and observed specific rotation to the data observed for (1S,5R)-1-(3,4-dichlorophenyl)-3-azabicyclo[3.1.0]hexane as the reference sample.

The assignment of the absolute configuration of the title compound was confirmed by a single crystal X-ray structure obtained from a crystal of (1S,5R)-1-[4-(trifluoromethyl)phenyl]-3-azabicyclo[3.1.0]hexane, (S)-(+)-mandelic acid salt. Both, analysis based on the known configuration of the (S)(+)-mandelic acid and on the basis of anomalous dispersion effects confirmed the assignment of the title compound as being (1S,5R)-1-[4-(trifluoromethyl)phenyl]-3-azabicyclo[3.1.0]hexane.

NMR ($^1$H, CDCl$_3$): δ 7.51 (d, 2H), 7.25 (d, 2H), 3.20 (d, 1H), 3.0-3.1 (m, 3H), 1.69 (m, 1H), 0.8-1.0 (m, 2H), NH not observed. MS (m/z): 228.1 [MH]$^+$.

Analytical Chromatography

Column: chiralcel OD 10 um, 250×4.6 mm

Mobile phase: A: n-Hexane; B: Isopropanol +0.1% Isopropyl amine

Gradient: isocratic 2% B

Flow rate: 1 mL/min

UV wavelengh range: 200-400 nm

Analysis time 25 min

| ret. time (min) | % a/a | |
|---|---|---|
| 16.5 | 0.4 | (1R,5S)-1-[4-(trifluoromethyl)phenyl]-3-azabicyclo[3.1.0]hexane |
| 21.7 | 99.6 | title compound |

Specific Optical Rotation: [α]$_D$ = −10° (CDCl$_3$, T = 20° C., c ≅ 0.004 g/0.8 mL).

Preparation 12: (1S,5R)-3-(3-Chloropropyl)-1-[4-(trifluoromethyl)phenyl]-3-azabicyclo[3.1.0]hexane

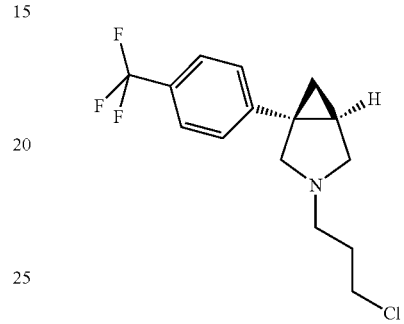

To a solution of (1S,5R)-1-[4-(trifluoromethyl)phenyl]-3-azabicyclo[3.1.0]hexane (1.00 g) in dry tetrahydrofuran (5 mL), diisopropylethylamine (2.4 mL) and 1-bromo-3-chloropropane (3.7 mL) were added and the resulting mixture was heated at reflux for 3 hours. After cooling at room temperature it was diluted with ethyl acetate (30 mL) washed twice with a saturated solution of NH$_4$Cl in water (20 mL) and once with a saturated solution of NaHCO$_3$ in water (20 mL), dried over anhydrous Na$_2$SO$_4$ and concentrated under reduced pressure. The crude product was purified by silica gel chromatography eluting with cyclohexane/EtOAc 7:3 to give the title compound as a colourless oil (1.26 g).

NMR ($^1$H, CDCl$_3$): δ 7.50 (d, 2H) 7.19 (d, 2H), 3.59 (t, 2H), 3.33 (d, 1H), 3.09 (d, 1H), 2.58 (m, 2H), 2.66 (dd, 1H), 2.46 (dd, 1H), 1.92 (m, 2H), 1.74 (m, 1H), 1,67 (t, 1H), 0.81 (dd, 1H). MS (m/z): 304 [MH]$^+$.

Example 1

3-(3-{[4-methyl-5-(4-methyl-1,3-oxazol-5-yl)-4H-1,2,4-triazol-3-yl]thio}propyl)-(1R,5S/1S,5R )-1-[4-(pentafluoro-λ$^6$-sulfanyl)phenyl]-3-azabicyclo[3.1.0] hexane hydrochloride

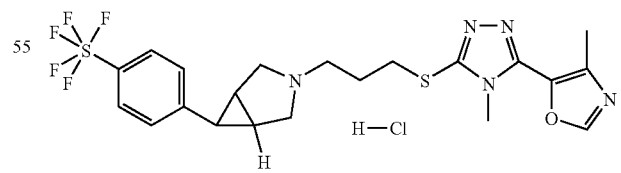

A mixture of (1R,5S/1S,5R)-1-[4-(pentafluoro-λ$^6$-sulfanyl)phenyl]-3-azabicyclo[3.1.0]hexane (38 mg), 3-[(3-chloropropyl)thio]-4-methyl-5-(4-methyl-1,3-oxazol-5-yl)-4H-1,2,4-triazole (0.17 mmol, Preparation 4), Na$_2$CO$_3$ (0.17 mmol) and NaI (0.13 mmol) in DMF (anhydrous, 0.5 mL) was heated at 60° C. for 24 h. H$_2$O was added and the mixture was extracted with ethyl acetate. The organic layer was dried over Na$_2$SO$_4$, filtered and the filtrate was concentrated in vacuo. The crude product was purified by flash chromatography (dichloromethane/MeOH from 97/3 to 95/5) to give 34 mg of the free base of the title compound. To a solution of this material in dichloromethane (0.2 mL) was added 0.065 mmol of HCl (1M in Et$_2$O), the solvent evaporated under vacuo and the material thus obtained triturated with Et$_2$O to give 32 mg of the title compound as a white slightly hygroscopic solid (43% yield).

NMR ($^1$H, DMSO): δ 10.44 (b,1H), 8.57 (s, 1H), 7.86 (d, 2H), 7.48 (d, 2H), 4.06 (m, 1H), 3.73 (dd, 1H), 3.68 (s, 3H), 3.63 (t, 1H), 3.51 (bt, 1H), 3.37 (t, 2H), 3.27 (s, 3H), 2.3 (m, 1H), 2.16 (m, 2H), 1.69 (t, 1H), 1.21 (t, 1H). MS (m/z): 522 [MH]$^+$.

Example 1 was separated to give the single enantiomers by semi-preparative HPLC using a chiral column Chiralpak AD-H 5 μm, 250×21 mm, eluent A: n-hexane; B:ethanol+0.1% isopropylamine, gradient isocratic 40% B, flow rate 6 ml/min, detection UV at 270 nm, analysis time 60 min. Retention times given were obtained using an analytical HPLC using a chiral column Chiralpak AD-H 5 μm, 250×4.6 mm, eluent A: n-hexane; B:ethanol+0.1% isopropylamine, gradient isocratic 40% B, flow rate 0.8 ml/min, detection UV at 200-400 nm, analysis time 25 min.

Enantiomer 1 was recovered in 24 mg yield as white solid (y=39%) from the racemate (120 mg). Rt.=17.3 min.

Enantiomer 2 was recovered in 47 mg yield as white solid (y=76%) from the racemate (120 mg). Rt.=19.6 min.

Enantiomer 2 showed a pKi value at the dopamine D3 receptor 10 fold higher than Enantiomer 1.

Example 2

(1R,5S/1S,5R)-3-(3-{[4-methyl-5-(4-methyl-1,3-oxazol-5-yl)-4H-1,2,4-triazol-3-yl]thio}propyl)-1-[3-(pentafluoro-λ$^6$-sulfanyl)phenyl]-3-azabicyclo[3.1.0]hexane hydrochloride

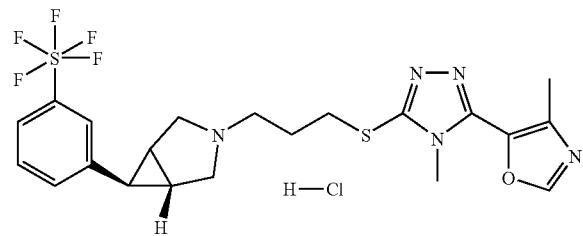

The title compound was prepared in analogy to the method described for Example 1 in 110 mg yield as a white slightly hygroscopic solid from 1-[3-(pentafluoro-λ$^6$-sulfanyl)phenyl]-3-azabicyclo[3.1.0]hexane (109 mg).

NMR ($^1$H, DMSO): δ 10.32 (bs,1H), 8.56 (m, 1H), 7.80 (m, 2H), 7.58 (m, 2H), 4.08 (m, 1H), 3.73 (m, 1H), 3.68 (s, 3H), 3.56 (m, 2H), 3.32 (m, 2H), 3.26 (m, 2H), 2.36 (s, 3H), 2.28 (m, 1H), 2.15 (m, 2H), 1.61 (m, 1H), 1.20 (m, 1H). MS (m/z): 522 [MH]$^+$.

Example 2 was separated to give the separated enantiomers by semi-preparative HPLC using a chiral column Chiralpak AD-H 5 μm, 250×21 mm, eluent A: n-hexane; B:ethanol+0.1% isopropylamine, gradient isocratic 15% B, flow rate 8 ml/min, detection UV at 270 nm, analysis time 60 min. Retention times given were obtained using an analytical HPLC using a chiral column Chiralpak AD-H 5 μm, 250×4.6 mm, eluent A: n-hexane; B:ethanol+0.1% isopropylamine, gradient isocratic 15% B, flow rate 1 ml/min, detection UV at 200-400 nm, analysis time 20 min.

Enantiomer 1 was recovered in 33 mg yield as white solid from the racemate (102 mg). Rt.=14.4 min.

Enantiomer 2 was recovered in 33 mg yield as white solid from the racemate (102 mg). Rt.=16.4 min.

Enantiomer 2 showed a pKi value at the dopamine D3 receptor 30 fold higher than Enantiomer 1.

Example 3

(1S,5R)-3-[3-({4-methyl-5-[4-(pentafluoro-λ$^6$-sulfanyl)phenyl]-4H-1,2,4-triazol-3-yl}thio)propyl]-1-[4-(trifluoromethyl)phenyl]-3-azabicyclo[3.1.0]hexane hydrochloride

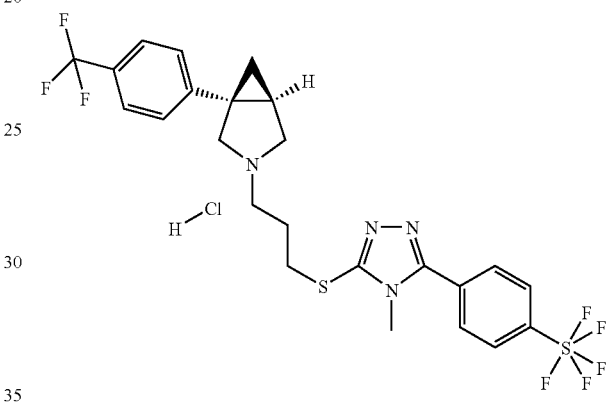

To a solution of the 3-thio-5-aryl-1,2,4-triazole (0.131 mmol) in dry acetonitrile (2 ml) 2-tert-butylimino-2-diethylamino-1,3-dimethyl-perhydro-1,3,2-diaza-phosphorine on polystyrene (90 mg, 2.2 mmol/g) was added and the resulting mixture was shaken for 30 minutes at room temperature then (1S,5R)-3-(3-chloropropyl)-1-[4-(trifluoromethyl)phenyl]-3-azabicyclo[3.1.0]hexane (40 mg) was added and the resulting mixture was shaken at 50° C. overnight. After cooling the resin was filtered off, washed with methanol (2 ml) and then the solvent was removed under reduced pressure. Purifications were carried out using mass directed HPLC:

Preparative Chromatographic Conditions
Column: X Terra MS C18 5 □m, 100×19 mm
Mobile phase: A: NH4HCO3 sol. 10 mM, pH10; B: CH3CN
Gradient: 30% (B) for 1 min, from 30% (B) to 95% (B) in 12 min, 95% (B) for 3 min
Flow rate: 17 ml/min
UV wavelength range: 210-350 nm
Mass range: 100-900 amu
Ionization: ES+

Then solvent was removed under reduced pressure to give compounds as a free base. The residue was taken up with dichloromethane (2 ml) and a 1.0 N HCl solution in diethylether was added (0.131 mmol) then solvent was removed under reduced pressure to give title compounds hydrochloride salt.

Analytical Chromatographic Conditions
Column: X Terra MS C18 5 μm, 50×4.6 mm
Mobile phase: A: NH4HCO3 sol. 10 mM, pH10; B: CH3CN Gradient: 30% (B) for 1 min, from 30% (B) to 95% (B) in 9 min, 95% (B) for 3 min
Flow rate: 1 ml/min
UV wavelength range: 210-350 nm
Mass range: 100-900 amu
Ionization: ES+
Analytical Data
Retention time=9.07 min
NMR ($^1$H, DMSO): δ=10.55 (bs, HCl), 8.06 (d, 2H), 7.94 (d, 2H), 7.64 (d, 2H), 7.45 (d, 2H), 4.03 (m, 1H), 3.70 (m, 1H), 3.63 (s, 3H), 3.58 (m, 1H), 3.28 (m, 5H), 2.26 (m, 1H), 2.14 (m, 2H), 1.69 (m, 1H), 1.16 (m, 1H).
MS (m/z): 585 [MH]$^+$

The invention claimed is:
1. A compound of formula (I) or a pharmaceutically acceptable salt thereof:

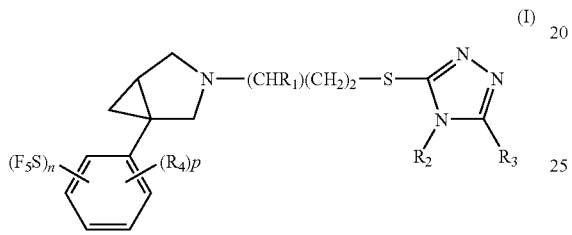

wherein
$R_1$ is hydrogen or $C_{1-4}$alkyl;
$R_2$ is $C_{1-4}$alkyl;
$R_3$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl and $SF_5$;
p is 0, 1, 2, 3 or 4; and
$R_4$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy and $C_{1-4}$alkanoyl;
n is 0 or 1;
wherein when $R_4$ is chlorine and p is 1, such $R_4$ is not present in the ortho position with respect to the linking bond to the rest of the molecule;
and wherein, if n is 0, $R_3$ comprises at least one $SF_5$ group as a substituent.

2. A stereochemical isomer enriched in the (1S,5R) configuration of formula (IA):

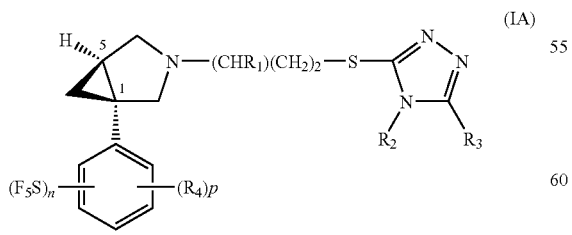

wherein $R_1$, $R_2$, $R_3$, $R_4$, n and p are defined in claim 1, or a pharmaceutically acceptable salt thereof 3. A compound as claimed in claim 1 having a formula (IB):

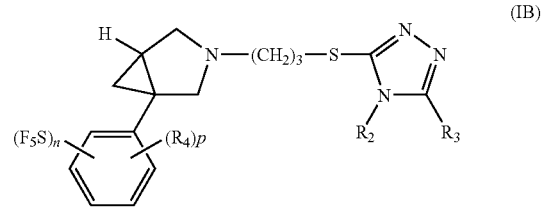

wherein $R_2$, $R_3$, $R_4$, n and p are as defined in claim 1, or a pharmaceutically acceptable salt thereof 4. A stereochemical isomer enriched in the (1S,5R) configuration of formula (IB)':

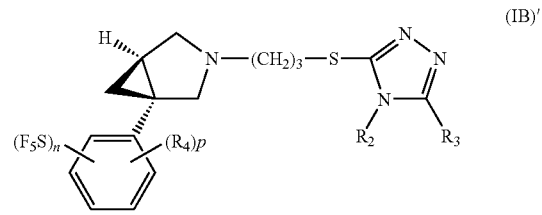

or a pharmaceutically acceptable salt thereof, wherein $R_2$, $R_3$, $R_4$, n and p are as defined in claim 1.
5. A compound as claimed in claim 1 wherein $R_2$ is methyl.
6. A compound as claimed in claim 1 wherein $R_3$ is phenyl, 4-trifluoromethyl-phenyl, 3,4-difluorophenyl, or 4-pentafluorosulfanylphenyl), or 4-methyl-1,3-oxazol-5-yl, 2-methyl-5-trifluoromethy-1,3-oxazol-4-yl, or an 3-methyl-5-isoxazolyl.
7. A compound as claimed in claim 1 wherein $R_4$ is trifluoromethyl.
8. A compound as claimed in claim 1 wherein p is 0.
9. A compound as claimed in claim 1 wherein n is 0 and $R_3$ is 4-pentafluorosulfanylphenyl.
10. A compound as claimed in claim 1 which is:
3-(3-{[4-methyl-5-(4-methyl-1,3-oxazol-5-yl)-4H-1,2,4-triazol-3-yl]thio}propyl) -(1R,5S/1S,5R)-1-[4-(pentafluoro-λ$^6$-sulfanyl)phenyl]-3-azabicyclo[3.1.0]hexane;
3-(3-{[4-methyl-5-(4-methyl-1,3-oxazol-5-yl)-4H-1,2,4-triazol-3-yl]thio}propyl)-(1S,5R) -1-[4-(pentafluoro-λ$^6$-sulfanyl)phenyl]-3-azabicyclo[3.1.0]hexane;
(1R,5S/1S,5R)-3-(3-{[4-methyl-5-(4-methyl-1,3-oxazol-5-yl)-4H-1,2,4-triazol-3-yl]thio}propyl)-1-[3-(pentafluoro-λ$^6$-sulfanyl)phenyl]-3-azabicyclo[3.1.0]hexane;
(1S,5R)-3-(3-{[4-methyl-5-(4-methyl-1,3-oxazol-5-yl)-4H-1,2,4-triazol-3-yl]thio}propyl)-1-[3-(pentafluoro-λ$^6$-sulfanyl)phenyl]-3-azabicyclo[3.1.0]hexane;
(1S,5R)-3-[3-({4-methyl-5-[4-(pentafluoro-λ$^6$-sulfanyl)phenyl]-4H-1,2,4-triazol-3-yl}thio)propyl]-1-[4-(trifluoromethyl)phenyl]-3-azabicyclo[3.1.0]hexane;
or a pharmaceutically acceptable salt thereof.
11. A pharmaceutical composition comprising a compound as claimed in claim 1 or a pharmaceutically acceptable salt thereof and a pharmaceutically acceptable carrier.

* * * * *